United States Patent
Fang

(10) Patent No.: US 6,787,743 B2
(45) Date of Patent: Sep. 7, 2004

(54) APPARATUS FOR THE PRODUCTION OF GINKGO LEAF TEA

(76) Inventor: Pao-Hsien Fang, 156 Common St., Belmont, MA (US) 02478

( * ) Notice: Subject to any disclaimer, the term of this patent is extended or adjusted under 35 U.S.C. 154(b) by 60 days.

(21) Appl. No.: 10/038,275

(22) Filed: Jan. 4, 2002

(65) Prior Publication Data
US 2003/0127454 A1 Jul. 10, 2003

(51) Int. Cl.$^7$ ................................................ H05B 6/64
(52) U.S. Cl. ....................................... 219/678; 219/707
(58) Field of Search ................................. 219/678, 707, 219/705, 492, 697; 426/597, 271, 435, 456, 429, 590, 431; 424/752, 770; 34/492

(56) References Cited

U.S. PATENT DOCUMENTS 4,350,860 A * 9/1982 Ueda .......................... 219/705
4,379,964 A * 4/1983 Kanazawa et al. .......... 219/492
4,631,380 A * 12/1986 Tran ............................ 219/697
4,660,298 A * 4/1987 Nambu et al. ................ 34/492

* cited by examiner

Primary Examiner—Quang T. Van

(57) ABSTRACT

Ginkgo leaves contain many beneficial chemicals which can be transferred into a preparation of tea. However, the leaves contain 2-hexenal, a chemical which is toxic and has an unpleasant taste. Therefore, removal of the 2-hexenal is an essential step for the tea production. This removal is accomplished in this invention by a microwave apparatus, which has the advantage of a rapid rate of treatment at great energy efficiency. Therefore, this invention provides an effective means for large scale ginkgo leaf tea production.

10 Claims, 3 Drawing Sheets

Apparatus for production of Gingko Leaf Tea

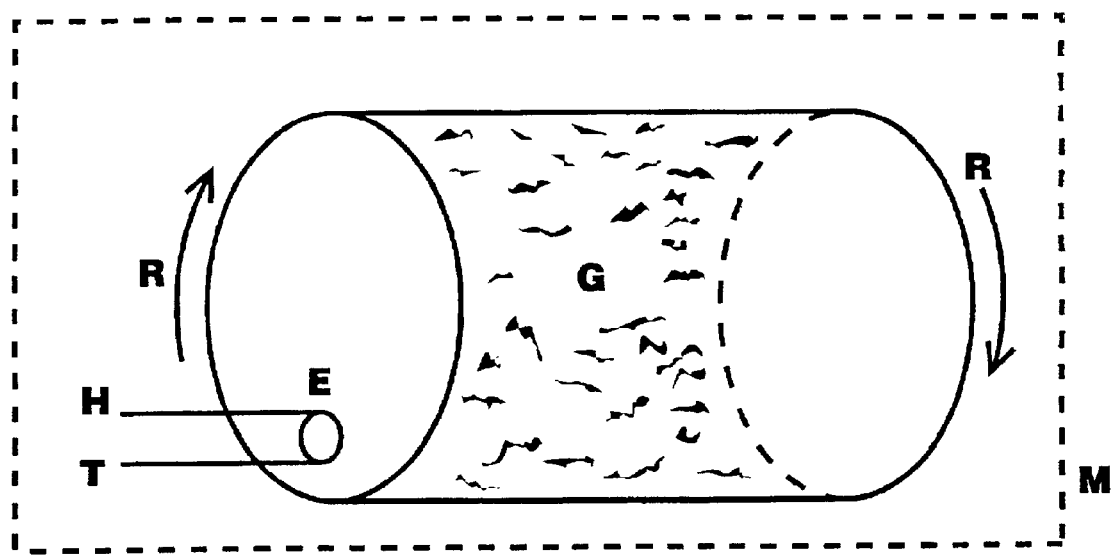
Figure 1. Apparatus for production of Gingko Leaf Tea

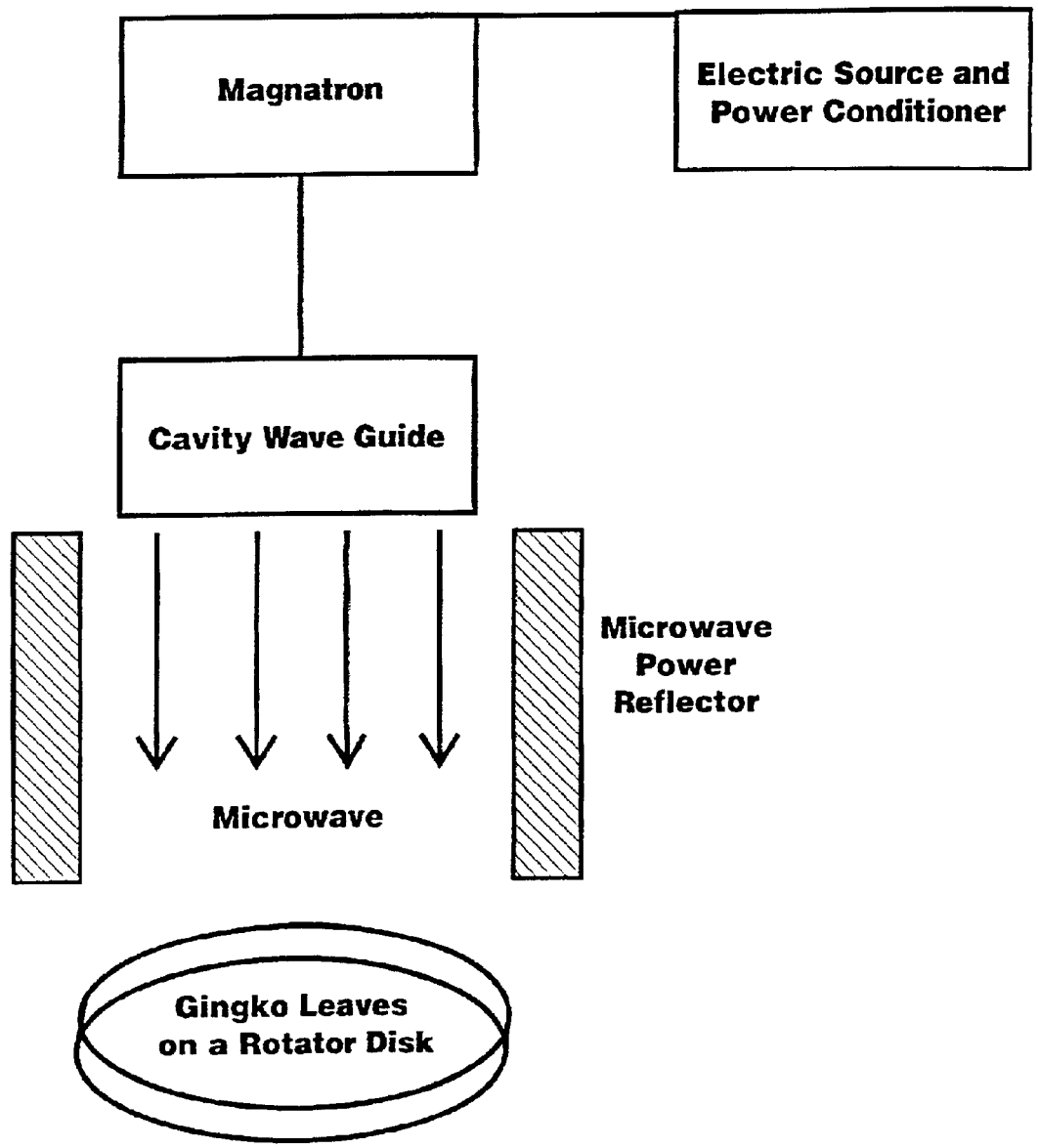
Figure 2. Apparatus for production of Gingko Leaf Tea

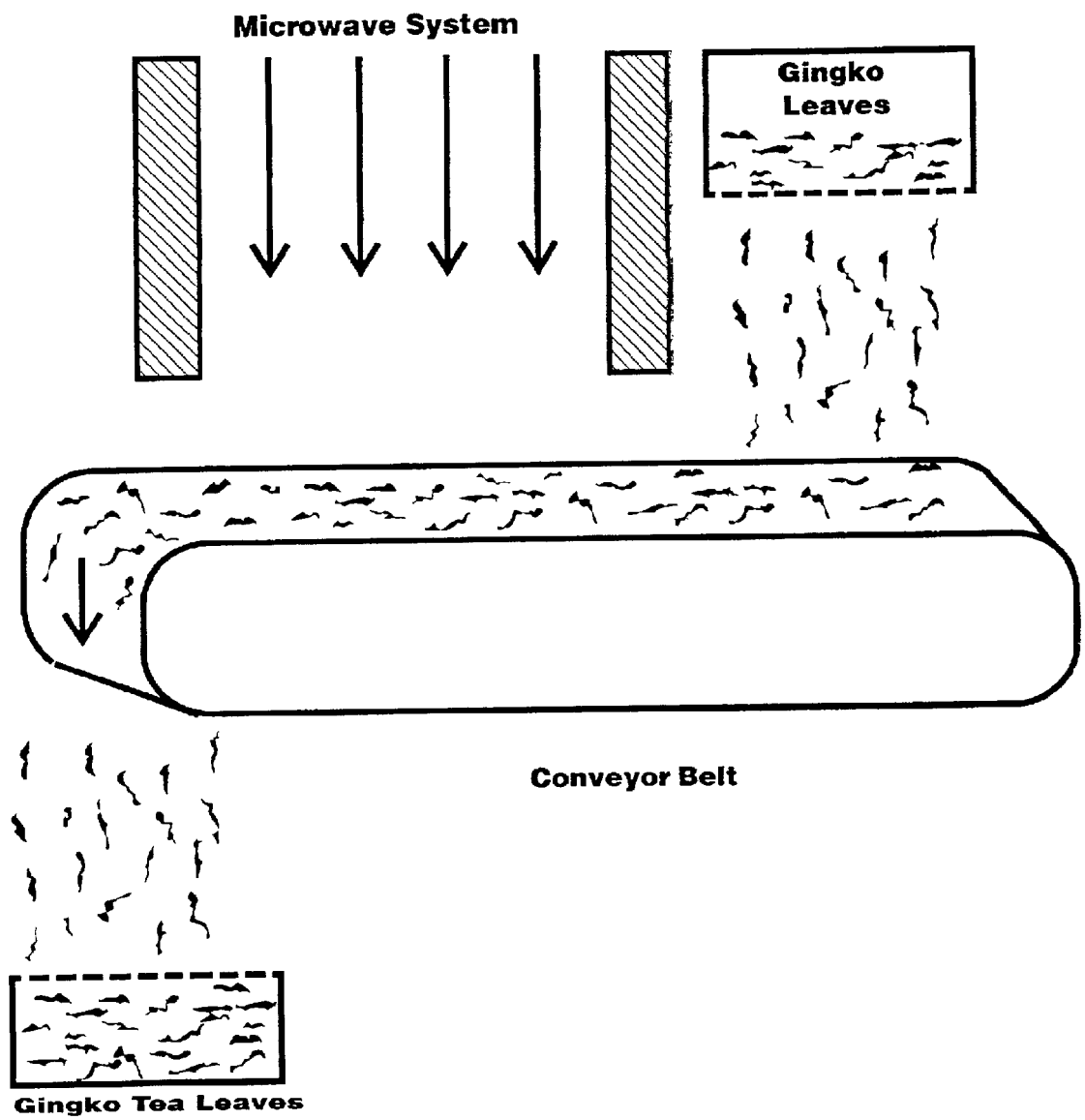
Figure 3. Apparatus for production of Gingko Leaf Tea

APPARATUS FOR THE PRODUCTION OF GINKGO LEAF TEA

BACKGROUND OF THE INVENTION

The utility of ginkgo biloba leaves has received wide attention in recent years, ranging from simple drink stuff to nutritional supplement and medicinal agent. The present invention is related to the ginkgo tea, specifically it is concerned with the removal of the 2-hexenal from the initial ginkgo leaves to produce a safe and palatable substance. Toward this objective, a patent exists (U.S. Pat. No. 5,888,571, Mar. 30, 1999, Inventor: Seung Chang Choi). Choi's process involves thermal treatment at various temperature ranges at various time intervals, which are consequently time consuming and energy wasting. The present invention is to eliminate these defects through a microwave irradiation. Other benefits will also be described in the present invention.

BRIEF DESCRIPTION OF THE INVENTION

A presently known method to eliminate 2-hexenal for producing ginkgo leaf tea is given by the 1999 patent of Choi (U.S. Pat. No. 5,888,571). The principle is a thermal decomposition of 2-hexenal. In this process, the raise of the leaf temperature is by roasting through an indirect heat transfer between the wall of the roaster and the ginkgo leaves, and the contact among the assembly of the leaves. An objective of the present invention is to utilize a different principle for the decomposition of 2-hexenal based on a direct interaction between the ginkgo leaves and the microwave energy. Therefore, the energy is invested principally in the strategic material, namely the ginkgo leaves, where energy is required to achieve the treatment. Consequently, a massive energy consumption involved in the thermal process is eliminated. At the same time, the temperature can be raised as well as dropped rapidly, therefore the thermal lag is practically eliminated. The result will be an efficient controlled system in which both mechanical efficiency and the medicinal efficacy can be expected at the same time with an energy economy.

DETAILED DESCRIPTION OF THE INVENTION

The production of ginkgo tea in this invention consists of (1) construction of the apparatus for the tea production and (2) method of the operation, and will be described sequentially.

(1) The construction of the apparatus is schematically presented in FIG. 1. As a general description, the material for the system should be non-metallic and minimum microwave absorptive. Microwave absorption should be allowed only by the ginkgo leaves, wherein the leaves become the microwave power absorber, consequently, a self heat producer.

The legends of FIG. 1 are as follows:
(1) M: Microwave power chamber
(2) R: Rotator
(3) G: Ginkgo leaves material
(4) E: Exhauster
(5) H: Humidity sensor
(6) T: Temperature sensor.

Following are the explanations:
(1) M is a primary component of this system, which supplies the energy for the ginkgo treatment and provides a space where the ginkgo material is to be processed.

(2) R is a rotator with a rotisserie action. In addition, R will provide a continuous motion of the ginkgo material to result in a uniformity of the product. The diameter of R is determined by the desired production volume. The volume of R should be two to ten times that of the volume of loose ginkgo leaves. The extra volume is provided for free motion of the ginkgo leaves such that the leaves would be wholly exposed to the microwave.

(3) G, the ginkgo leaf pieces to be treated.

(4) E is an exhauster tubing to remove the moisture originated from the water and 2-hexenal contained in G. The tubing diameter is about the same to one hundredth of G.

(5) H is a humidity sensor to monitor the water vapor and the vapor of 2-hexenal evoluted from G through the treatment. The sensor is placed at the outlet of E.

In the operation of the apparatus, the following steps are involved:

I) The microwave chamber (1) consists of a microwave generator and provides a microwave ambient when the chamber becomes operative.

ii) The rotator R is a hollow cylinder with a provision of a controllable rate or rotation. The ginkgo leaves are introduced directly into R or first shredded into pieces of about 0.1 to 1 cm dimension prior to placing into R.

iii) The system R is sufficiently closed to prevent an intrusion of external atmosphere and the escape of microwave to the outside environment. The content of oxygen, nitrogen and other components in the atmosphere could interact with the chemicals of ginkgo to effect the integrity of its chemicals. The enclosure construction becomes possible with the present invention utilizing microwave agent and is inconvenient or difficult in the method of Choi cited as a reference of the present invention. In fact, in a part of Choi's patent, nitrogen is introduced at 90 to 100 degrees C. for 30 to 40 minutes. The role of nitrogen is presumably to protect ginkgo from the atmospheric interference. In the present invention, the system is a closure system and the required treatment time is a fraction of one minute to five minutes, therefore, the elaborate protection is not required.

iv) The ordinary 2-hexenal has a boiling point of 146 degree C. This point is determined from a macro-quantity of pure material. In ginkgo leaves, the 2-hexenal is a highly dispersed minor component, the temperature could be depressed to a much lower value due to a direct interaction between the molecular 2-hexenal and the microwave. The evolution of 2-hexenal can be monitored through several approaches, such as the humidity, electrical impedance or chemical property of the evoluted 2-hexenal. For example. When the humidity is plotted as a function of the treatment time, initially, a rapid rise of humidity is expected due to the water contribution which has a much lower boiling point than that of 2-hexenal. In the progress of the treatment, a secondary rise in humidity will occur due to the evolution of 2-hexenal. An eventual vanishing of the additional humidity signifies an exhaustion of 2-hexenal in ginkgo and a completion of the treatment process.

In practice, the control through monitor of iv) can be substituted by an experienced person with an observation of the smell and color of the leaves under treatment. The color is dependent on the degree of humidity in the pre-treated gingko leaves, the microwave power and the treatment time.

In fact, the color can also be dictated by personal preferences. The smell is a stronger indication and more directly related to the evolution and the elimination of 2-hexenal. The smell can be best perceived by a comparison with a known 2-hexenal specimen.

For additional treatment to render a brittle consistency of ginkgo leaves to facilitate tea powder, additional treatment time at a reduced microwave power can be made. The parameter depends on the system configuration, the water content and other conditions of the ginkgo leaves and can be determined through a trial experiment. The tea powder can be made by grinding the post-treated tea leaves. In addition, the treatment time can be prolonged for a period of one to one hundred seconds. In one case, the tea leaves are to be completely pulverized. In another form, the tea substance is only partially pulverized and after the material has been sieved and separated into a portion of fine powder of 0.01 to 1 millimeter diameter, it is placed in a paper bag as a powder tea. The remaining coarse tea pieces are to be used in the other form of tea preparation by introducing the tea substance in the hot or boiled water, in the preference of the habit of tea drinkers.

In the above, a basic apparatus has been disclosed in FIG. 1. Two variations of the apparatus of FIG. 1 are disclosed below.

I) A batch process apparatus is presented in FIG. 2. In this Figure, the microwave system is more explicitly illustrated. For a simpler construction, a rotating disk is used instead of the rotator of FIG. 1. For a limited quantity of leaves, this system would be satisfactory.

ii) FIG. 3 is for a continuous assembly production system, wherein both raw gingko leaves feeding and gingko tea leaves retriever are in one larger chamber. Microwave radiation into the environment is minimized by a judicious metallic reflector arranged at strategic positions. Ar the same time, due to an attenuation of the microwave radiation at larger distance, a larger chamber would be beneficial.

In the following, three examples will be presented as a guide for the operation of the apparatus to produce the material for the tea preparation.

EXAMPLE (1)

Tea leaves preferably fresh or one, or ultimately three days collected from the gingko tree are subjected to rinsing with water. Subsequently, the superficial water on the leaves is removed with a colander and the leaves are allowed to dry in ventilated air for a period of one to ten hours. Next, the leaves are transferred to the microwave chamber and the microwave power is turned on after the rotator is in motion at the rate of one tenth to one rotation per second. At the end of the pre-designated time, the microwave power is turned off and the leaves are removed for use in tea preparation.

EXAMPLE (2)

The gingko leaves in Example (1) are shredded or cut into small pieces of 0.1 to 3 centimeter in conformity with the familiar tea leaves and then percolated in hot or boiled water for a period of time in minutes depending on the preference of the tea drinker.

EXAMPLE (3)

For some tea drinkers, the preferred form of tea is powder enclosed in a microscopically perforated paper bag.

For extraction of various materials such as flavonoids, high flavonoids and proanthocyanidins for pharmaceutical processing, a removal of 2-hexenal as a precursor for the extraction is desirable. The present invention thus provides a means to manufacture the precursor.

I claim:

1. An apparatus to remove 2-hexenal from ginkgo leaves, said apparatus comprising
    (1) a microwave power chamber,
    (2) a rotator
    (3) ginkgo leave acceptance
    (4) an exhauster comprising an extension tube of the rotator having a narrower diameter than that of the rotator
    (5) humidity sensor and
    (6) temperature sensor.

2. The microwave power chamber of claim 1 comprises a microwave generator and a chamber with microwave environment.

3. The rotator of claim 1 comprises a hollow cylinder having a controllable rate of rotation.

4. The ginkgo leaves of claim 1 are shredded pieces of 0.1 to 3 centimeters in dimension.

5. The 2-hexenal sensor of claim 1 comprises a humidity sensor located near the exhauster.

6. The temperature sensor of claim 1 is made of a thermal sensor located near the exhauster.

7. The apparatus of claim 1, wherein the rotator of claim 3 is replaced by a rotating disk plate to simplify the mechanical construction.

8. The apparatus of claim 1 wherein a ginkgo leaves feeder is incorporated in a conveyor belt for a facilitation of an assembly production.

9. The apparatus of claim 1, wherein the treated ginkgo leaves retriever is incorporated in a conveyor belt for facilitation of an assembly production.

10. The apparatus of claim 1 for the production of precursors of ginkgo extracts free from 2-hexenal.

* * * * *